United States Patent [19]

Gray et al.

[11] Patent Number: 5,801,021
[45] Date of Patent: Sep. 1, 1998

[54] AMPLIFICATIONS OF CHROMOSOMAL REGION 20Q13 AS A PROGNOSTIC INDICATOR IN BREAST CANCER

[75] Inventors: Joe W. Gray, San Francisco; Colin Collins, San Rafael; Daniel Pinkel, Walnut Creek, all of Calif.; Olli-Pekka Kallioniemi; Minna M. Tanner, both of Tampere, Finland

[73] Assignee: The Regents of the University of California, Oakland, Calif.

[21] Appl. No.: 546,130

[22] Filed: Oct. 20, 1995

[51] Int. Cl.⁶ .................... C12Q 1/68; C07H 21/04; C07H 21/00
[52] U.S. Cl. .................... 435/94.2; 435/6; 536/24.3; 536/25.32; 536/26.6
[58] Field of Search .................... 435/6, 91.2; 536/24.3, 536/26.6, 25.32

[56] References Cited

U.S. PATENT DOCUMENTS 5,472,842  12/1995  Stokke et al. .................... 435/6

FOREIGN PATENT DOCUMENTS 0 571 911 A2  12/1993  European Pat. Off.

OTHER PUBLICATIONS

Strokke et al., *Genomics*, 26:134 (1995).
Tanner et al., *Cancer Research*, 54:4257 (1994).
Gyapay et al. The 1993–1994 genethon human genetic linkage map. Nature Genetics. Jun. 1994, vol. 7, pp. 246–339.
Datebase EST–STS on MPsrch Accession No. G08049, Murray et al. Cooperative human linkage center 08 Aug. 1995.

*Primary Examiner*—Kenneth R. Horlick
*Assistant Examiner*—Joyce Tung
*Attorney, Agent, or Firm*—Townsend and Townsend and Crew

[57] ABSTRACT

The present invention relates to in situ hybridization methods for the identification of new chromosomal abnormalities associated with various diseases. In particular, it provides probes which are specific to a region of amplification in chromosome 20.

44 Claims, 4 Drawing Sheets

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

TTGGCATTGG TATCAGGTAG CTG        2 3

( 2 ) INFORMATION FOR SEQ ID NO:2:

( i ) SEQUENCE CHARACTERISTICS:

(A) LENGTH: 24 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:2:

TTGGAGCAGA GAGGGGATTG TGTG        24

(2) INFORMATION FOR SEQ ID NO:3:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:3:

AATCCCCTCA AACCTGCTG CTAC        24

(2) INFORMATION FOR SEQ ID NO:4:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:4:

TGGAGCCTGA ACTTCTGCAA TC        22

(2) INFORMATION FOR SEQ ID NO:5:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:5:

CCGGGATACC GACATTG        17

(2) INFORMATION FOR SEQ ID NO:6:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:6:

TGCACATAAA ACAGCCAGC        19

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:7:

TTGGAATCAA TGGAGCAAAA　　　　　　　　　　　　　　　　　　　　　　　　20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:8:

AGCTTTACCC AATGTGGTCC　　　　　　　　　　　　　　　　　　　　　　　　20

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:9:

GTGGTGAACA CCAATAAATG G　　　　　　　　　　　　　　　　　　　　　　21

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:10:

AAGCAAATAA AACCAATAAA CTCG　　　　　　　　　　　　　　　　　　　　24

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:11:

CAAGATCTGA CCCCGTCAAT C　　　　　　　　　　　　　　　　　　　　　　21

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:12:

GACTTCTTCA GGAAAGAGAT CAGTG　　　　　　　　　　　　　　　　　　　25

( 2 ) INFORMATION FOR SEQ ID NO:13:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

GCCATGTACC CACCTGAAAA ATC                                23

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

TCAGAACACC CGTGCAGAAT TAAG                             24

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

CCTAAAACTT GGTGCTTAAA TCTA                             24

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

GTCTCACAAG GCAGATGTGG                                    20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

TTTGTGTATG TTGAGCCATC                                    20

( 2 ) INFORMATION FOR SEQ ID NO:18:

( i ) SEQUENCE CHARACTERISTICS:

(A) LENGTH: 22 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:18:

CTTCCAATCT CATTCTATGA GG    22

(2) INFORMATION FOR SEQ ID NO:19:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:19:

GCTTGTTTAA GTGTCACTAG GG    22

(2) INFORMATION FOR SEQ ID NO:20:

(i) SEQUENCE CHARACTERISTICS:
                (A) LENGTH: 23 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:20:

CACTCTGGTA AATGACCTTT GTC    23

(2) INFORMATION FOR SEQ ID NO:21:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:21:

CCTACACCAT TCCAACTTTG G    21

(2) INFORMATION FOR SEQ ID NO:22:

(i) SEQUENCE CHARACTERISTICS:
                (A) LENGTH: 25 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:22:

GCCAGATGTA TGTTTGCTAC GGAAC    25

(2) INFORMATION FOR SEQ ID NO:23:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (i i) MOLECULE TYPE: DNA (x i) SEQUENCE DESCRIPTION: SEQ ID NO:23:

TCTCAAACCT GTCCACTTCT TG 22

(2) INFORMATION FOR SEQ ID NO:24:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:24:

CTGCTGTGGT GGAGAATGG 19

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:25:

TGTCCTCCTT CTCCCTCATC CTAC 24

(2) INFORMATION FOR SEQ ID NO:26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:26:

AATGCCTCCA CTCACAGGAA TG 22

(2) INFORMATION FOR SEQ ID NO:27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:27:

CCTCTTCAGT GTCTTCCTAT TGA 23

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:28:

GGGAGGAGGT TGTAGGCAAC 20

( 2 ) INFORMATION FOR SEQ ID NO:29:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

AGCAAAGCAA AGGTGGCACA C　　　　　　　　　　　　　　　　21

( 2 ) INFORMATION FOR SEQ ID NO:30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

TGACATGGGA GAAGACACAC TTCC　　　　　　　　　　　　　24

( 2 ) INFORMATION FOR SEQ ID NO:31:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:31:

AGGTTTACCA ATGTGTTTGG　　　　　　　　　　　　　　　　20

( 2 ) INFORMATION FOR SEQ ID NO:32:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

TCTACATCCC ATTCTCTTCT G　　　　　　　　　　　　　　　21

AMPLIFICATIONS OF CHROMOSOMAL REGION 20Q13 AS A PROGNOSTIC INDICATOR IN BREAST CANCER

BACKGROUND OF THE INVENTION

This invention pertains to the field to the field of cytogenetics. More particularly this invention pertains to the identification of a amplification at about 20q13 that is a good prognosite indicator of various cancers. In addition, this invention provides a number of probes specific for the 20q13 amplicon.

This invention was made with Government support under Grant Nos. CA-528207 and CA-44768 awarded by the National Institutes of Health and Contract Nos. DE-AC-03-76SF00098, W-7405-ENG-48 and W-7405-ENG-36 awarded by the U.S. Department of Energy. The Government has certain rights in this invention.

Chromosome abnormalities are often associated with genetic disorders, degenerative diseases, and cancer. In particular, the deletion or multiplication of copies of whole chromosomes or chromosomal segments, and higher level amplifications of specific regions of the genome are common occurrences in cancer. See, for example Smith, et al., *Breast Cancer Res. Treat.*, 18: Suppl. 1: 5–14 (1991, van de Vijer & Nusse, *Biochim. Biophys. Acta.* 1072: 33–50 (1991), Sato, et al., *Cancer Res.*, 50: 7184–7189 (1990). In fact, the amplification and deletion of DNA sequences containing proto-oncogenes and tumor-suppressor genes, respectively, are frequently characteristic of tumorigenesis. Dutrillaux, et al., *Cancer Genet. Cytogenet.*, 49: 203–217 (1990). Clearly the identification of amplified and deleted regions and the cloning of the genes involved is crucial both to the study of tumorigenesis and to the development of cancer diagnostics.

The detection of amplified or deleted chromosomal regions has traditionally been done by cytogenetics. Because of the complex packing of DNA into the chromosomes, resolution of cytogenetic techniques has been limited to regions larger than about 10 Mb; approximately the width of a band in Giemsa-stained chromosomes. In complex karyotypes with multiple translocations and other genetic changes, traditional cytogenetic analysis is of little utility because karyotype information is lacking or cannot be interpreted. Teyssier, J. R., *Cancer Genet. Cytogenet.*, 37: 103 (1989). Furthermore conventional cytogenetic banding analysis is time consuming, labor intensive, and frequently difficult or impossible.

More recently, cloned probes have been used to assess the amount of a given DNA sequence in a chromosome by Southern blotting. This method is effective even if the genome is heavily rearranged so as to eliminate useful karyotype information. However, Southern blotting only gives a rough estimate of the copy number of a DNA sequence, and does not give any information about the localization of that sequence within the chromosome.

Comparative genomic hybridization (CGH) is a more recent approach to identify the presence and localization of amplified/deleted sequences. See Kallioniemi, et al., *Science*, 258: 818 (1992). CGH, like Southern blotting, reveals amplifications and deletions irrespective of genome rearrangement. Additionally, CGH provides a more quantitative estimate of copy number than Souther blotting, and moreover also provides information of the localization of the amplified or deleted sequence in the normal chromosome.

Using CGH, the chromosomal 20q13 region has been identified as a region that is frequently amplified in cancers (see, e.g. copending application U.S. Ser. No. 08/132,808, filed on Oct. 6, 1993). Initial analysis of this region in breast cancer cell lines identified a region approximately 2 Mb on chromosome 20 that is consistently amplified.

SUMMARY OF THE INVENTION

The present invention relates to the identification of a narrow region (about 600 kb) within a 2 Mb amplicon located at about chromosome 20q13 (more precisely at 20q13.2) that is consistently amplified in primary tumors. In addition this invention provides a contig (a series of clones that contiguously spans this amplicon) as well as sequence information for a large number of exons and cDNAs located within the contig. The contig or components thereof can be used to prepare probes specific for the amplicon. The probes can be used to detect chromosomal abnormalities at 20q13.

Thus, in one embodiment, this invention provides a method of detecting a chromosome abnormality (e.g., an amplification or a deletion) at about position FLpter 0.825 on human chromosome 20 (20q13.2). The method involves contacting a chromosome sample from a patient with a composition consisting essentially of one or more labeled nucleic acid probes each of which binds selectively to a target polynucleotide sequence at about position FLpter 0.825 on human chromosome 20 under conditions in which the probe forms a stable hybridization complex with the target sequence; and detecting the hybridization complex. The step of detecting the hybridization complex can involve determining the copy number of the target sequence. The probe preferably comprises a nucleic acid that specifically hybridizes under stringent conditions to a nucleic acid selected from the nucleic acids listed in Table 1 or Table 2. Even more preferably, the probe is one or more nucleic acids selected from the nucleic acids listed in Table 1 or Table 2. The probe is preferably labeled, and is more preferably labeled with digoxigenin or biotin. In one embodiment, the hybridization complex is detected in interphase nuclei in the sample. Detection is preferably carried out by detecting a fluorescent label (e.g., FITC, fluorescein, or Texas Red). The method can further involve contacting the sample with a reference probe which binds selectively to a chromosome 20 centromere.

In another embodiment, this invention provides for probes that specifically bind to the 20q13 amplicon. Thus, this invention provides for a composition comprising a labeled nucleic acid probe which binds selectively to a target polynucleotide sequence at about FLpter 0.825 on human chromosome 20. The probes comprise one or more nucleic acids selected from the group consisting of the nucleic acids listed in Table 1 or Table 2. In a preferred embodiment, the probes are labelled with digoxigenin or biotin.

This invention also provides for kits for the detection of a chromosomal abnormality at about position FLpter 0.825 on human chromosome 20. The kits include a compartment which contains a labeled nucleic acid probe which binds selectively to a target polynucleotide sequence at about FLpter 0.825 on human chromosome 20. The probe preferably includes at least one nucleic acid that specifically hybridizes under stringent conditions to a nucleic acid selected the nucleic acids listed in Table 1 or Table 2. Even more preferably, the probes comprise one or more nucleic acids selected from the nucleic acids listed in Table 1 or Table 2. In a preferred embodiment, the probes are labelled with digoxigenin or biotin. The kit may further include a reference probe specific to a sequence in the centromere of chromosome 20.

Definitions

A "chromosome sample" as used herein refers to a tissue or cell sample prepared for standard in situ hybridization methods described below. The sample is prepared such that individual chromosomes remain substantially intact and typically comprises metaphase spreads or interphase nuclei prepared according to standard techniques.

"Nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

"Subsequence" refers to a sequence of nucleic acids that comprise a part of a longer sequence of nucleic acids.

A "probe" or a "nucleic acid probe", as used herein, is defined to be a collection of one or more nucleic acid fragments whose hybridization to a target can be detected. The probe is labeled as described below so that its binding to the target can be detected. The probe is produced from a source of nucleic acids from one or more particular (preselected) portions of the genome, for example one or more clones, an isolated whole chromosome or chromosome fragment, or a collection of polymerase chain reaction (PCR) amplification products. The probes of the present invention are produced from nucleic acids found in the 20q13 amplicon as described herein. The probe may be processed in some manner, for example, by blocking or removal of repetitive nucleic acids or enrichment with unique nucleic acids. Thus the word "probe" may be used herein to refer not only to the detectable nucleic acids, but to the detectable nucleic acids in the form in which they are applied to the target, for example, with the blocking nucleic acids, etc. The blocking nucleic acid may also be referred to separately. What "probe" refers to specifically is clear from the context in which the word is used.

"Hybridizing" refers the binding of two single stranded nucleic acids via complementary base pairing.

"Bind(s) substantially" or "binds specifically" or "binds selectively" or "hybridizing specifically to" refers to complementary hybridization between an oligonucleotide and a target sequence and embraces minor mismatches that can be accommodated by reducing the stringency of the hybridization media to achieve the desired detection of the target polynucleotide sequence. These terms also refer to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Typically, stringent conditions will be those in which the salt concentration is at least about 0.02 Na ion concentration (or other salts) at pH 7.0 to 8.3 and the temperature is at least about 60° C. for short probes. Stringent conditions may also be achieved with the addition of destabilizing agents such as formamide.

One of skill will recognize that the precise sequence of the particular probes described herein can be modified to a certain degree to produce probes that are "substantially identical" to the disclosed probes, but retain the ability to bind substantially to the target sequences. Such modifications are specifically covered by reference to the individual probes herein. The term "substantial identity" of polynucleotide sequences means that a polynucleotide comprises a sequence that has at least 90% sequence identity, more preferably at least 95%, compared to a reference sequence using the methods described below using standard parameters.

Two nucleic acid sequences are said to be "identical" if the sequence of nucleotides in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Another indication that nucleotide sequences are substantially identical is if two molecules hybridize to the same sequence under stringent conditions. Stringent conditions are sequence dependent and will be different in different circumstances. Generally, stringent conditions are selected to be about 5° C. lower than the thermal melting point $(T_m)$ for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar or lower at pH 7 and the temperature is at least about 60° C.

DETAILED DESCRIPTION

This invention provides a number of nucleic acid probes useful for the detection of chromosomal abnormalities at 20q13. Studies using comparative genomic hybridization (CGH) have shown that a region at chromosome 20q13 is increased in copy number frequently in cancers of the breast (~30%), ovary (~15%), bladder (~30%), head and neck (~75%) and colon (~80%). This suggests the presence of one or more genes that contribute to the progression of several solid tumors are located at 20q13.

Gene amplification is one mechanism by which dominantly acting oncogenes are overexpressed, allowing tumors to acquire novel growth characteristics and/or resistance to chemotherapeutic agents. Loci implicated in human breast cancer progression and amplified in 10–25% of primary breast carcinomas include the erbB-2 locus (Lupu et al., *Breast Cancer Res. Treat.*, 27: 83 (1993), Slamon et al. *Science*, 235: 177–182 (1987), Heiskanen et al. *Biotechniques*, 17: 928 (1994)) at 17q12, cyclin-D (Mahadevan et al., *Science*, 255: 1253–1255 (1993), Gillett et al., *Canc. Res.*, 54: 1812 (1994)) at 11q13 and MYC (Gaffey et al., *Mod. Pathol.*, 6: 654 (1993)) at 8q34.

Pangenomic surveys using comparative genomic hybridization (CGH) recently identified about 20 novel regions of increased copy number in breast cancer (Kallioniemi et al., *Genomics*, 20: 125–128 (1994)). One of these loci, band 20q13, was amplified in 18% of primary tumors and 40% of cell lines (Kallioniemi et al., *Genomics*, 20: 125–128 (1994)). More recently, this same region was found amplified in 15% of ovarian, 80% of bladder and 80% of colorectal tumors. The resolution of CGH is limited to 5–10 Mb. Thus, FISH was performed using locus specific probes to confirm the CGH data and precisely map the region of amplification.

The 20q13 region has been analyzed in breast cancer at the molecular level and a region, approximately 600 kb wide, that is consistently amplified was, identified, as described herein. Moreover, as shown herein, the importance of this amplification in breast cancer is indicated by the strong association between amplification and decreased patient survival and increased tumor proliferation (specifically, increased fraction of cells in S-phase).

Figure 1A:
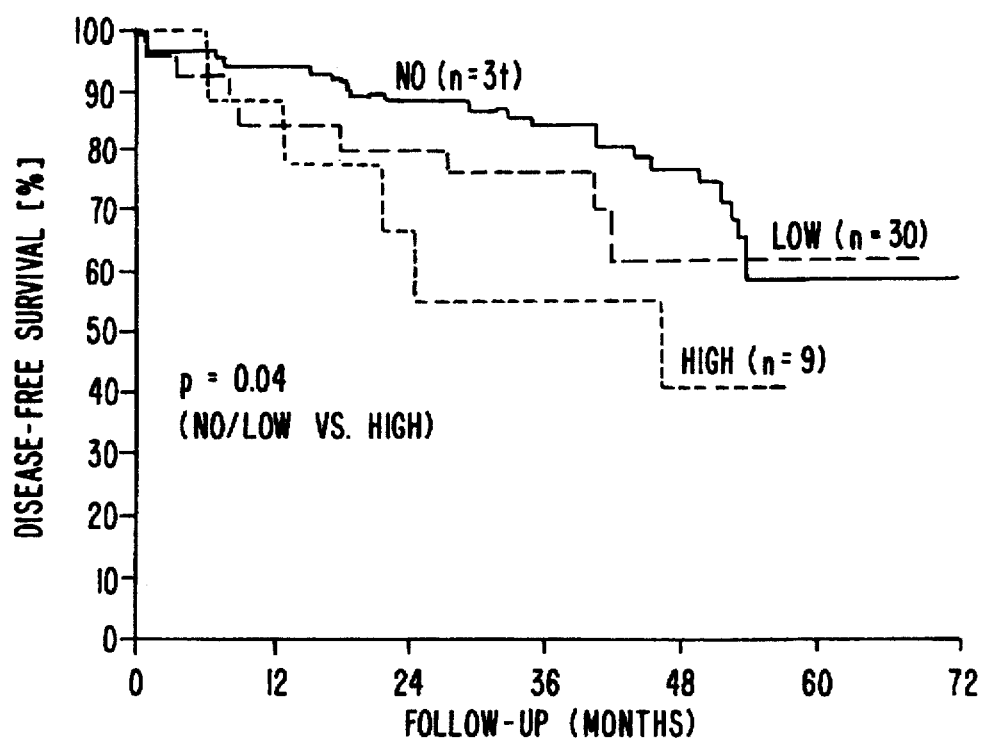
FIG. 1(A) shows disease-free survival of 129 breast cancer patients according to the level of 20q13 amplification. Patients with tumors having high level 20q13 amplification have a shorter disease-free survival (p=0.04 by Mantel-Cox test) compared to those having no or low level amplification.
Figure 1B:
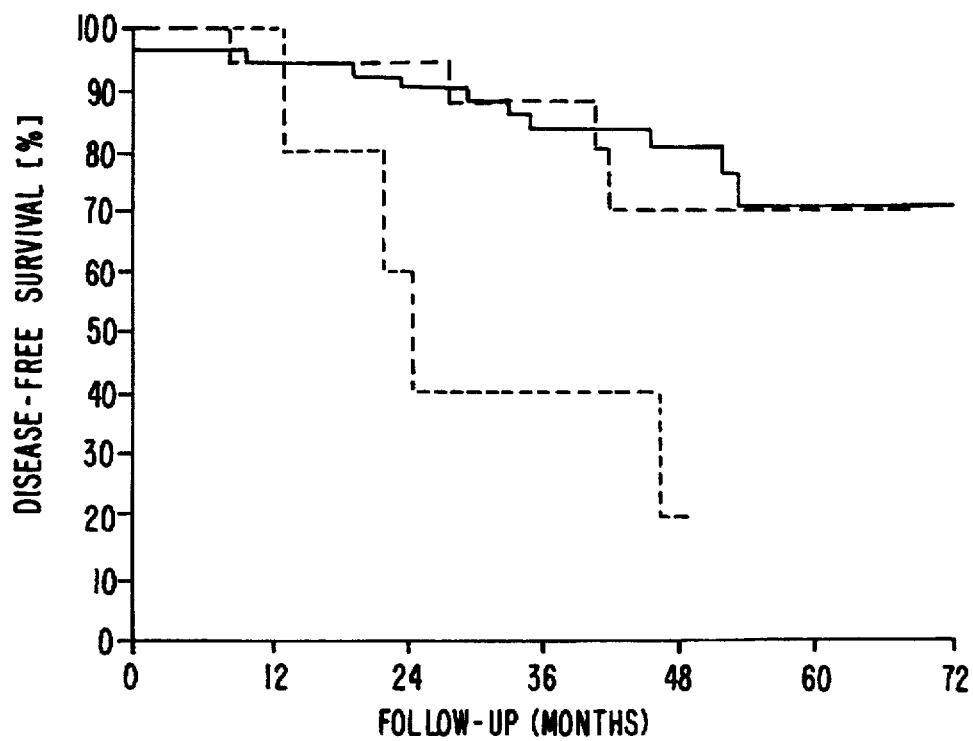
FIG. 1(B) Shows the same disease-free survival difference of FIG. 4(A) in the sub-group of 79 axillary node-negative patients (p=0.0022 by Mantel-Cox test).
Figure 2:
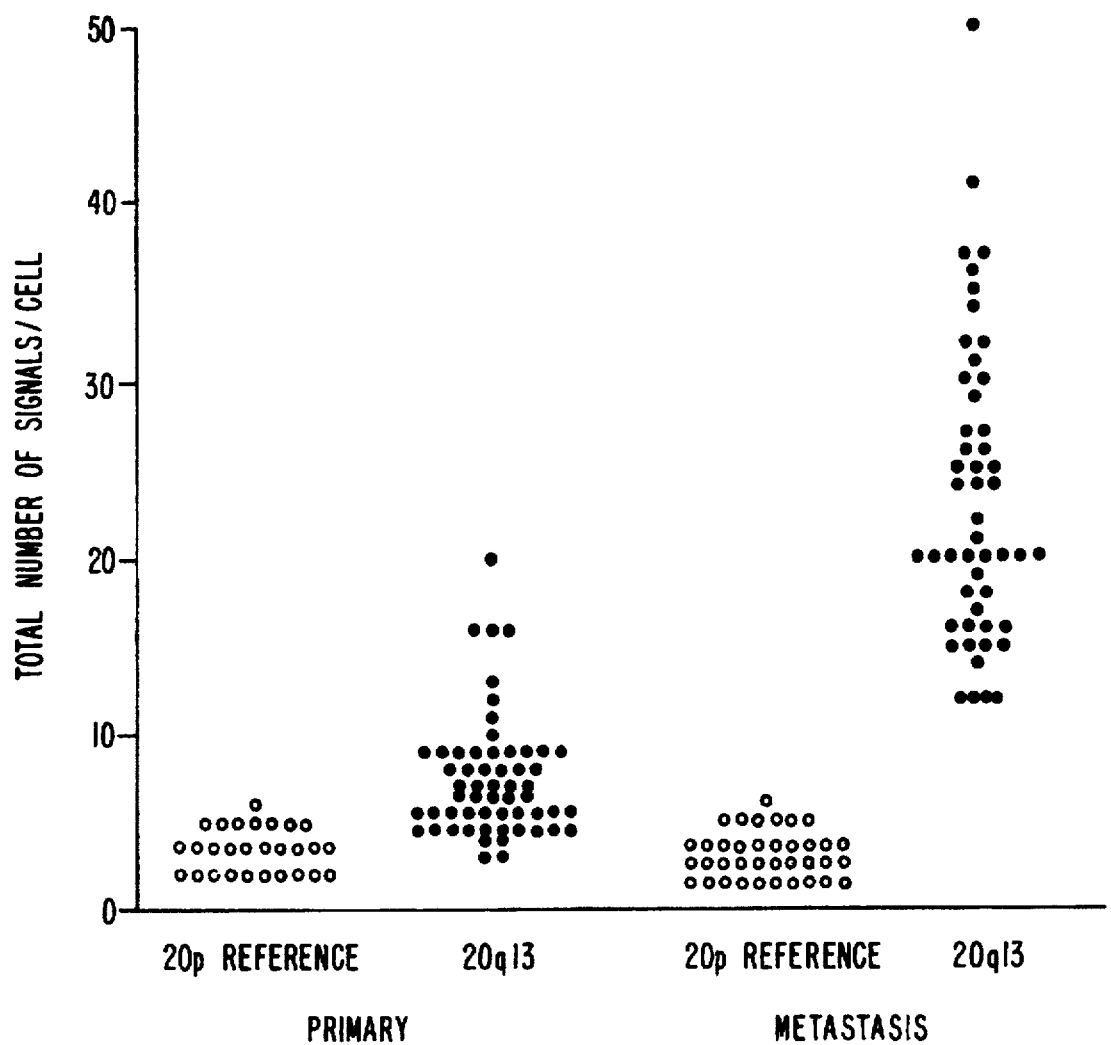
FIG. 2 shows a comparison of 20q13 amplification detected by FISH in a primary breast carcinoma and its metastasis from a 29-year patient. A low level amplification of 20q13 (20q13 compared to 20p reference probe) was found in the primary tumor. The metastasis, which appeared 8 months after mastectomy, shows a high level amplification of the chromosome 20q13 region. The overall copy number of chromosome 20 (20p reference probe) remained unchanged. Each data point represents gene copy numbers in individual tumor cells analyzed.
Figure 3:
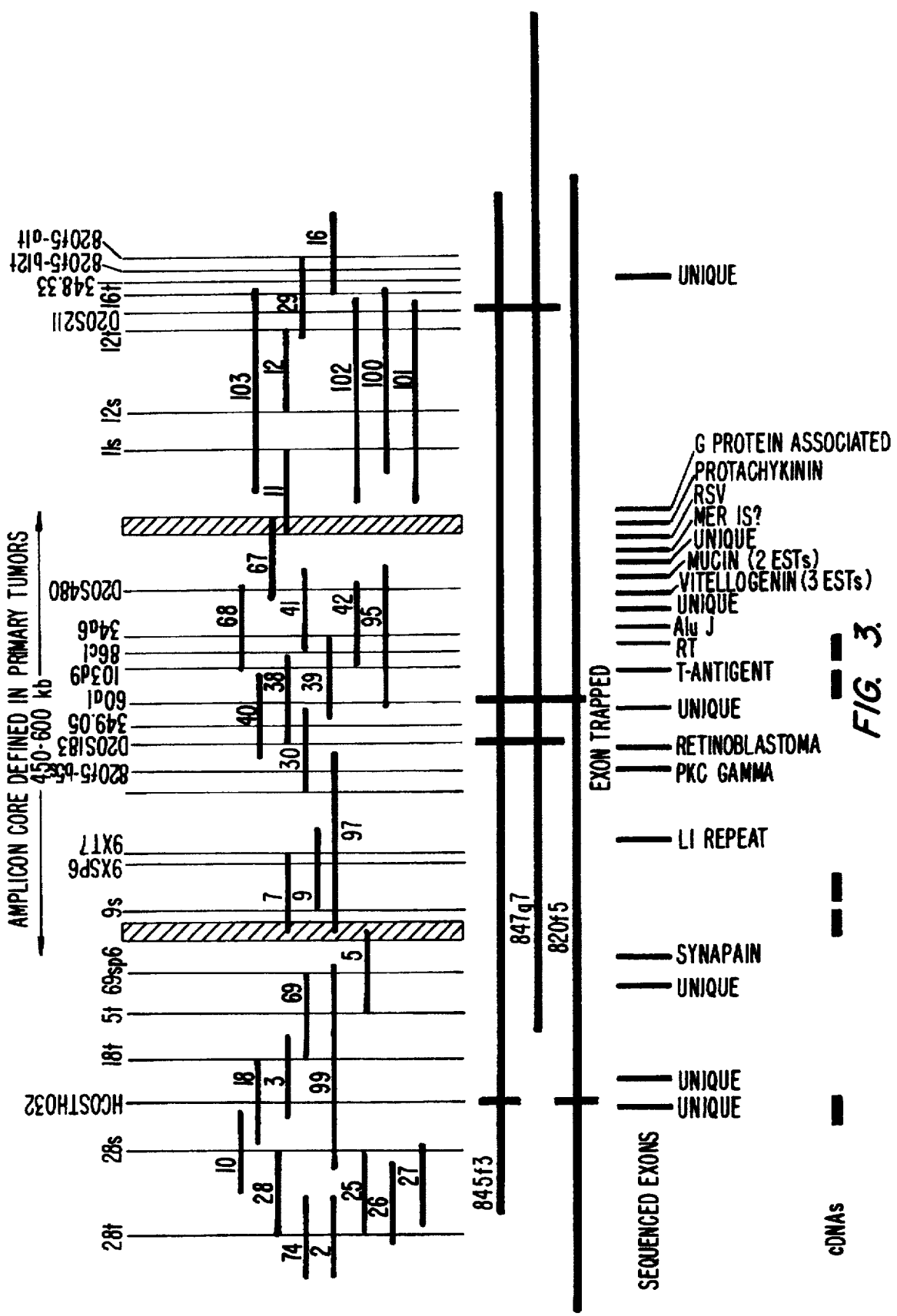
FIG. 3 shows a graphical representation of the molecular cytogenetic mapping and subsequent cloning of the 20q13.2 amplicon. Genetic distance is indicated in centiMorgans (cM). The thick black bar represents the region of highest level amplification in the breast cancer cell line BT474 and covers a region of about 1.5 Mb. P1 and BAC clones are represented as short horizontal lines and YAC clones as heavier horizontal lines. Not all YAC and P1 clones are shown. YACs 957f3, 782c9, 931h12, and 901b12 are truncated. Sequence tagged sites (STSs) appear as thin vertical lines and open circles indicate that a given YAC has been tested for and is positive for a given STS. Not all STSs have been tested on all YACs. The interval from which more than 100 exons have been trapped is represented as a filled box. The 600 kb interval spanning the region of highest amplification level in primary tumors is represented by the filled black box (labeled Sequence). The lower part of the figure shows the levels of amplification in two primary tumors that further narrow the region of highest amplification to within about 600 kb.

In particular, as explained in detail in Example 1, high-level 20q13 amplification was associated (p=0.0022) with poor disease free survival in node-negative patients, compared to cases with no or low-level amplification (FIG. 1). Survival of patients with moderately amplified tumors did not differ significantly from those without amplification. Without being bound to a particular theory, it is suggested that an explanation for this observation may be that low level amplification precedes high level amplification. In this regard, it may be significant that one patient developed a local metastasis with high-level 20q13.2 amplification 8 month after resection of a primary tumor with low level amplification (FIG. 3).

Figure 4:
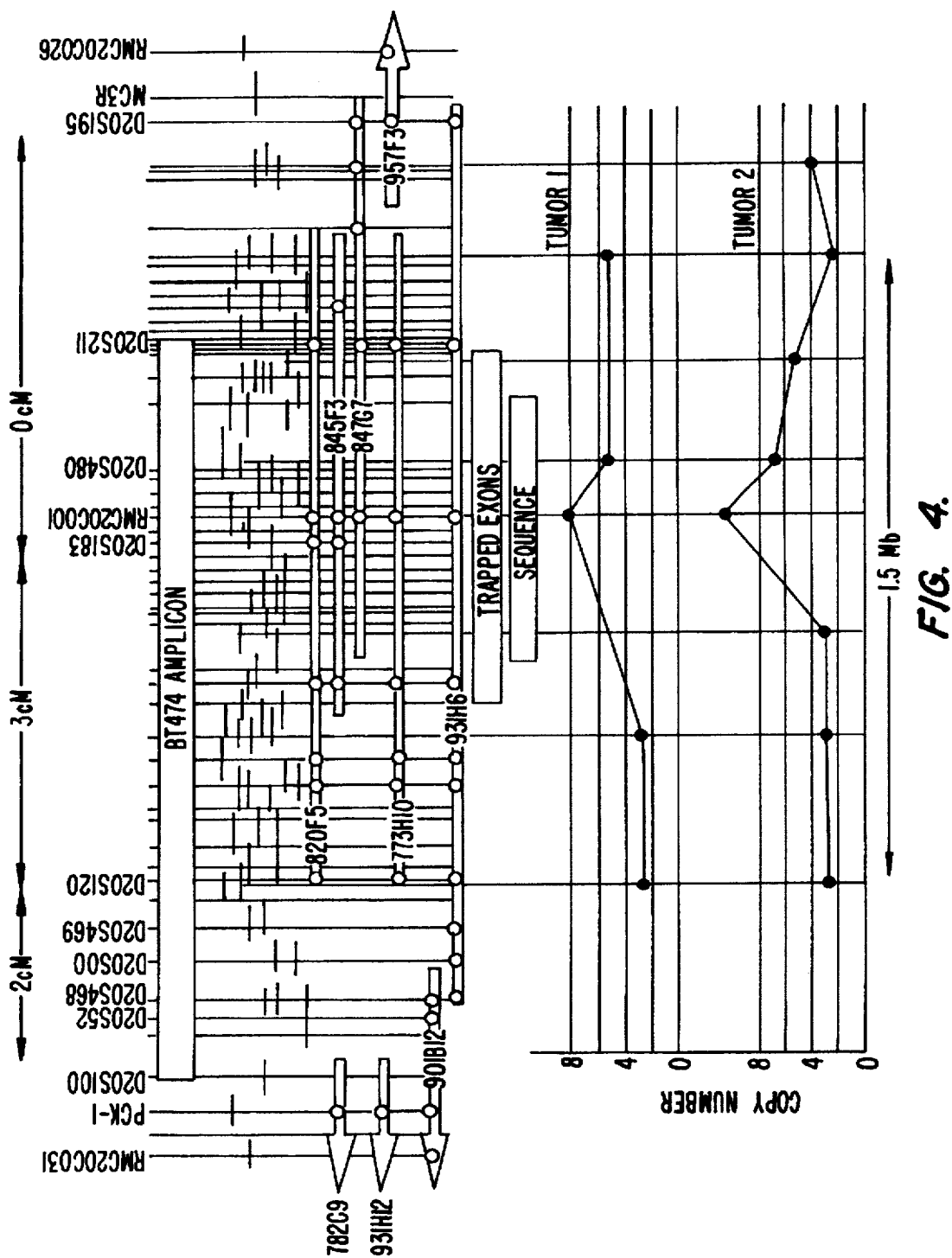
FIG. 4 provides a higher resolution map of the amplicon core as defined in primary tumors.

The 20q13 amplification was associated with high histologic grade of the tumors. This correlation was seen in both moderately and highly amplified tumors. There was also a correlation (p=0.0085) between high level amplification of a region complementary to a particular probe, RMC20C001 (Tanner et al., *Cancer Res.*, 54: 4257–4260 (1994)), and cell proliferation, measured by the fraction of cells in S-phase (FIG. 4). This finding is important because it identifies a phenotype that can be scored in functional assays, without knowing the mechanism underlying the increased S-phase fraction. The 20q13 amplification did not correlate with the age of the patient, primary tumor size, axillary nodal or steroid hormone-receptor status.

This work localized the 20q13.2 amplicon to an interval of approximately 2 Mb. Furthermore, it suggests that high-level amplification, found in 7% of the tumors, confers an aggressive phenotype on the tumor, adversely affecting clinical outcome. Low level amplification (22% of primary tumors) was associated with pathological features typical of aggressive tumors (high histologic grade, aneuploidy and cell proliferation) but not patient prognosis.

In addition, it is shown herein that the 20q13 amplicon (more precisely the 20q13.2 amplicon) is one of three separate co-amplified loci on human chromosome 20 that are packaged together throughout the genomes of some primary tumors and breast cancer cell lines. No known oncogenes map in the 20q13.2 amplicon.

Identification of 20q13 Amplicon Probes

Initially, a paucity of available molecular cytogenetic probes dictated that FISH probes be generated by the random selection of cosmids from a chromosome 20 specific library, LA20NC01, and map them to chromosome 20 by digital imaging microscopy. Approximately 46 cosmids, spanning the 70 Mb chromosome, were isolated for which fractional length measurements (FLpter) and band assignments were obtained. Twenty six of the cosmids were used to assay copy number in the breast cancer cell line BT474 by interphase FISH analysis. Copy number was determined by counting hybridization signals in interphase nuclei. This analysis revealed that cosmid RMC20C001 (Flpter, 0.824; 20q13.2), described by Stokke et al., *Genomics*, 26: 134–137 (1995), defined the highest-level amplification (~60 copies/cell) in BT474 cells (Tanner et al., *Cancer Res.*, 54: 4257–4260 (1994)).

P1 clones containing genetically mapped sequences were selected from 20q13.2 and used as FISH probes to confirm and further define the region of amplification. Other P1 clones were selected for candidate oncogenes broadly localized to the 20q13.2 region (Flpter, 0.81–0.84). These were selected from the DuPont P1 library (Shepherd, et al., *Proc. Natl. Acad. Sci. USA*, 92: 2629 (1994), available commercially from Genome Systems), by PCR (Saiki et al, *Science*, 230: 1350 (1985)) using primer pairs developed in the 3' untranslated region of each candidate gene. Gene specific P1 clones were obtained for, protein tyrosine phosphatase (PTPN1, Flpter 0.78), melanocortin 3 receptor (MC3R, Flpter 0.81), phosphoenolpyruvate carboxy kinase (PCK1, Flpter 0.85), zinc finger protein 8 (ZNF8, Flpter 0.93), guanine nucleotide-binding protein (GNAS 1, Flpter 0.873), src-oncogene (SRC, Flpter 0.669), topoisomerase 1 (TOP1, Flpter 0.675), the bcl-2 related gene bcl-x (Flpter 0.526) and the transcription factor E2F-1 (FLpter 0.541). Each clone was mapped by digital imaging microscopy and assigned Flpter values. Five of these genes (SRC, TOPO1, GNAS1, E2F-1 and BC1-x) were excluded as candidate oncogenes in the amplicon because they mapped well outside the critical region at Flpter 0.81–0.84. Three genes (PTPNR1, PCK-1 and MC3R) localized close enough to the critical region to warrant further investigation.

Interphase FISH on 14 breast cancer cell lines and 36 primary tumors using 24 cosmid and 3 gene specific P1 (PTPNRL, PCK-1 and MC3R) probes found high level amplification in 35% (5/14) of breast cancer cell lines and 8% (3/36) of primary tumors with one or more probe. The region with the highest copy number in 4/5 of the cell lines and 3/3 primary tumors was defined by the cosmid RMC20C001. This indicated that PTPNR1, PCK1 and MC3R could also be excluded as candidates for oncogenes in the amplicon and, moreover, narrowed the critical region from 10 Mb to 1.5–2.0 Mb (see, Tanner et al., *Cancer Res.*, 54: 4257–4260 (1994).

Because probe RMC20C001 detected high-level (3 to 10-fold) 20q13.2 amplification in 35% of cell lines and 8% of primary tumors it was used to (1) define the prevalence of amplification in an expanded tumor population, (2) assess the frequency and level of amplification in these tumors, (3) evaluate the association of the 20q13.2 amplicon with pathological and biological features, (4) determine if a relationship exists between 20q13 amplification and clinical outcome and (5) assess 20q13 amplification in metastatic breast tumors.

As detailed in Example 1, fluorescent in situ hybridization (FISH) with RMC20C001 was used to assess 20q13.2 amplification in 132 primary and 11 recurrent breast tumors. The absolute copy number (mean number of hybridization signals per cell) and the level of amplification (mean number of signals relative to the p-arm reference probe) were determined. Two types of amplification were found: Low level amplification (1.5–3 fold with FISH signals dispersed throughout the tumor nuclei) and high level amplification (>3 fold with tightly clustered FISH signals). Low level 20q13.2 amplification was found in 29 of the 132 primary tumors (22%), whereas nine cases (6.8%) showed high level amplification.

RMC20C001 and four flanking P1 probes (MC3R, PCK, RMC20C026, and RMC20C030) were used to study the extent of DNA amplification in highly amplified tumors. Only RMC20C001 was consistently amplified in all tumors. This finding confirmed that the region of common amplification is within a 2 Mb interval flanked by but not including PCK-1 and MC3R.

A physical map was assembled to further localize the minimum common region of amplification and to isolate the postulated oncogene(s). The DuPont P1 library (Shepherd et al. *Proc. Natl. Acad. Sci. USA*, 91: 2629 (1994) was screened for STSs likely to map in band 20q13.2. P1 clones at the loci D20S102, D20S100, D20S120, D20S183, D20S480, D20S211 were isolated, and FISH localized each to 20q13.2. Interphase FISH analysis was then performed in the breast cancer cell line BT474 to assess the amplification level at each locus. The loci D20S100-D20S120-D20S183-D20S480-D20S211 were highly amplified in the BT474 cell line, whereas D20S102 detected only low level amplification. Therefore, 5 STSs, spanning 5 cM, were localized within the 20q13.2 amplicon and were utilized to screen the CEPH megaYAC library.

CEPH megaYAC library screening and computer searches of public databases revealed D20S120-D20S183-D20S480-D20S211 to be linked on each of three megaYAC clones y820f5, 773h10, and 931h6 (FIG. 3). Moreover, screening the CEPH megaYAC library with STSs generated from the ends of cosmids RMC20C001, RMC20C30 and RMC20C028 localized RMC20C001 to each of the same three YAC clones. It was estimated, based on the size of the smallest of these YAC clones, that D20S120-D20S 183-RMC20C001-D20S480-D20S211 map into an interval of less than 1.1 Mb. D20S100 was localized 300 kb distal to D20S 120 by interphase FISH and to YAC901b12 by STS mapping. The combined STS data made it possible to construct a 12 member YAC contig which spans roughly 4 Mb encompassing the 1.5 Mb amplicon and containing the loci RMC20C030-PCK1-RMC20C001-MC3R-RMC20C026. Each YAC was mapped by FISH to confirm localization to 20q13.2 and to check for chimerism. Five clonal isolates of each YAC were sized by pulsed field gel electrophoresis (PFGE). None of the YACs are chimeric, however, several are highly unstable.

The YAC contig served as a framework from which to construct a 2 MbP1 contig spanning the 20Q13 amplicon. P1 clones offered numerous advantages over YAC clones including (1) stability, (2) a chimeric frequency of less than 1%, (3) DNA isolation by standard miniprep procedures, (4) they make ideal FISH probes, (5) the ends can be sequenced directly, (6) engineered γδ transposons carrying bidirectional primer binding sites can be integrated at any position in the cloned DNA (Strathmann et al., *Proc. Natl. Acad. Sci. USA*, 88: 1247 (1991)) (7) P1 clones are the templates for sequencing the human and Drosophila genomes at the LBNL HGC (Palazzolo et al. *DOE Human Genome Program, Contractor-Grantee Workshop IV.* Santa Fe, New Mex., Nov. 13–17 1994).

About 90 P1 clones were isolated by screening the DuPont P1 library either by PCR or filter hybridization. For PCR based screening, more than 22 novel STSs were created by two methods. In the first method, the ends of P1 clones localized to the amplicon were sequenced, STSs developed, and the P1 library screened for walking clones. In the second approach inter-Alu PCR (Nelson et al., 86: 6686–6690 (1989)) was performed on YACs spanning the amplicon and the products cloned and sequenced for STS creation. In the filter based hybridization scheme P1 clones were obtained by performing inter-Alu PCR on YACs spanning the amplicon, radio-labeling the products and hybridizing these against filters containing a gridded array of the P1 library. Finally, to close gaps a human genomic bacterial artificial chromosome (BAC) library (Shizuya et al. *Proc. Natl. Acad. Sci. USA*, 89: 8794 (1992), commercially available from Research Genetics, Huntsville, Alabama, USA) was screened by PCR. These methods combined to produce more than 100 P1 and BAC clones were localized to 20q13.2 by FISH. STS content mapping, fingerprinting, and free-chromatin fish (Heiskanen et al., *BioTechniques*, 17: 928 (1994)) were used to construct the 2 Mb contig shown in FIG. 3.

Fine Mapping the 20p13.2 Amplicon in BT474

Clones from the 2 Mb P1 contig were used with FISH to map the level of amplification at 20q13.2 in the breast cancer cell line BT474. 35 P1 probes distributed at regular intervals along the contig were used. The resulting data indicated that the region of highest copy number increase in BT474 occurs between D20S100 and D20S211, an interval of approximately 1.5 Mb. P1 FISH probes, in this interval, detect an average of 50 signals per interphase nuclei in BT474, while no, or only low level amplification, was detected with the P1 clones outside this region. Thus, both the proximal and distal boundaries of the amplicon were cloned.

Fine Mapping the 20p13.2 Amplicon in Primary Tumors

Fine mapping the amplicon in primary tumors revealed the minimum common region of high amplification that is of pathobiological significance. This process is analogous to screening for informative meiosis in the narrowing of genetic intervals encoding heritable disease genes. Analysis of 132 primary tumors revealed thirty-eight primary tumors that are amplified at the RMC20C001 locus. Nine of these tumors have high level amplification at the RMC20C001 locus and were further analyzed by interphase FISH with 8 P1s that span the ≈2 Mb contig. The minimum common region of amplification was mapped to a ≈600 kb interval flanked by P1 clones #3 and #12 with the highest level of amplification detected by P1 clone #38 corresponding to RMC20C001 (FIG. 4).

The P1 clones spanning the 600 kb interval of the 20q13 amplicon are listed in Table 1 which provides a cross-reference to the DuPont P1 library described by Shepherd, et al., *Proc. Natl. Acad. Sci. USA*, 92: 2629 (1994). These P1 probes are available commercially from Genetic Systems.

TABLE 1

Cross reference to probes of the DuPont P1 library (Shepherd, et al., Proc Natl. Acad. Sci. U.S.A., 92:2629 (1994) which is commercially available from Genomic Systems, St. Louis, Missouri, U.S.A.). PCR primers are illustrated for amplication of Sequence tag sites for each clone. In addition PCR conditions (Mg concentration and annealing temperature), as well as PCR product size, is provided. Size: PCR product Size; mM MgCl: Mg concentration; Ann.: Annealing temperature; P1: P1 probe ID number; PC: DuPont Library Plate Coordinates; SCA: DuPont Library Single Clone address; SEQ forward and SEQ-backward: forward and backward PCR primers, respectively; SEQ ID NO:-forward and SEQ ID NO:-backward: Sequence Listing SEQ ID NO: for forward and backward primers, respectively.

| PRIMER NAME | SIZE (bp) | mM MgCl | Ann. | P1 | PC | SCA | SEQ-forward | SEQ-backward | SEQ ID NO:-forward | SEQ ID NO:-backward |
|---|---|---|---|---|---|---|---|---|---|---|
| 352.32 | 136 | 1.5 | 52 | 20 | 103-e5 | 1228e | TTGGCATTGTATCAGGTAGCTG | TTGGAGCAGAGAGGGGATTGTGTG | 1 | 2 |
| 388.13 F1/B1 | 201 | 1.5 | 52 | 17 | 69g6 | 821 | AATCCCCTCAAACCCTGCTGCTAC | TGGAGCCTGAACTTCTGCAATC | 3 | 4 |
|  |  |  |  | 19 | 98f4 | 1167f |  |  |  |  |
| D20S183 | 270 | 3 | 48 | 30 |  | 124g6 | CCGGGATACCGACAATTG | TGCACATAAAACAGCCAGC | 5 | 6 |
|  |  |  |  | 40 | 24h1 | 276h |  |  |  |  |
| D20S211 1/2 | 135 | 1.5 | 52 | 29 | 119f4 | 1418f | TTGGAATCAATGGAGCAAAA | AGCTTTACCCAATGTGGTCC | 7 | 8 |
| D20S480 | 300 | 3 | 55 | 68 | 100d12 | 1199d2 | GTCGTGAACACCAATAAATGG | AAGCAAATAAAACCAATAAACTCG | 9 | 10 |
|  |  |  |  | 41 | 86c1 | 1020c |  |  |  |  |
|  |  |  |  | 42 | 103d9 | 1232d |  |  |  |  |
|  |  |  |  | 67 | 91b2 | 1081b9 |  |  |  |  |
| 9X-S96 hmF/hmB | 165 | 1.5 | 55 | 7 | 31d11 | 370d | CAAGATCTGACCCGTCAATC | GACTTCTTCAGGAAAGAGATCAGTG | 11 | 12 |
|  |  |  |  | 9 | 3519 | 416f |  |  |  |  |
| 11S-17 F2/B4 | 146 | 3 | 58 | 11 | 41b1 | 480b | GCCATGTACCCACCTGAAAAATC | TCAGAACACCCGTGCAGAATTAAG | 13 | 14 |
| 12T-T7 F2/B1 | 153 | 3 | 58 | 12 | 42c2 | 493c | CCTAAAACTTGGTGTCTAAAATCTA | GTCTCACAAGGCAGAGTGTCG | 15 | 16 |
| 28T F1/B1 | 219 | 1.5 | 52 | 74 |  | 888f2 | TTTGTGTATGTTGAGCCATC | CTTCCAATCTCATTCTATGAGG | 17 | 18 |
|  |  |  |  | 2 | 12c6 | 137c |  |  |  |  |
|  |  |  |  | 25 | 118c11 | 1413c |  |  |  |  |
|  |  |  |  | 26 | 118c11 | 1413c |  |  |  |  |
| 28S F1/B3 | 214 | 1.5 | 55 | 28 | 118g11 | 1413g | GCTTGTTTAAGTGTCACTAGGG | CACTCTGGTAAATGACCTTTGTC | 19 | 20 |
|  |  |  |  | 23 | 118c11 | 1413c |  |  |  |  |
|  |  |  |  | 27 | 118g11 | 1413g |  |  |  |  |
|  |  |  |  | 10 | 36f10 | 429f |  |  |  |  |
| 69S | 100 | 3 | 55 | 69 |  | 412b5 | CCTACACCATTCCAACTTTGG | GCCAGATGTATGTTTGCTACGGAAC | 21 | 22 |
|  |  |  |  | 5 | 23c1 | 264c |  |  |  |  |
| HSCOFH032 F/B | 129 | 1.5 | 55 | 3 | 12-E11 | 142e | TCTCAAACCTGTCCACTTCTTG | CTGCTGTGTGGAGAATGG | 23 | 24 |
|  |  |  |  | 18 | 77a10 | 921a |  |  |  |  |
| 60A1 | 191 | 1.5 | 58 | 36 | 112g8 | 1139g | TGTCCTCCTTCTCCCCTCATCCTAC | AATGCCTCCACTCACAGGAATG | 25 | 26 |
|  |  |  |  | 39 | 34a6 | 401a |  |  |  |  |
| 820F5A1T F1/B1 | 175 | 1.5 | 48 | 15 | 53c7 | 630c | CCTCTTCAGTGTCTTCCTATGA | GGGAGGAGGTTTGTAGGCAAC | 27 | 28 |
|  |  |  |  | 16 | 58b9 | 692b |  |  |  |  |

TABLE 2

Cross reference to probes of the BAC library. Clone # refers to the clone number provided, e.g., in FIG. 4, while the plate coordinates are the plate coordinates in the Research Genetics BAC library. Size: PCR product Size; mM MgCl: Mg concentration; Ann.: Annealing temperature; BAC #: BAC probe ID number; SEQ-forward and SEQ-backward: forward and backward PCR primers, respectively. SEQ ID NO:-forward and SEQ ID NO:-backward: Sequence Listing, SEQ ID NO: for forward and backward primers, respectively.

| PRIMER NAME | SIZE (bp) | mM MgCl | Ann. | BAC # | BAC Plate Coordinates | SEQ-forward | SEQ-backward | SEQ ID NO:-forward | SEQ ID NO:-backward |
|---|---|---|---|---|---|---|---|---|---|
| 18T F1/B1 | 156 | 3 | 62 | 99 | L11 plate 146 | AGCAAAGCAAAGGTGGCACAC | TGACATGGGAGAAGACACACTTCC | 29 | 30 |
| 9S F1/B1 | 214 | 1.5 | 55 | 97 | E8 plate 183 | AGGTTTACCAATGTGTTTGG | TCTACAATCCCATTCTCTTCTG | 31 | 32 |
| D20S480 | 300 | 3 | 55 | 95 | H15 plate 140 | GTGGTGAACACCAATAAATGG | AAGCAAATAAAACCAATAAAACTCG | 9 | 10 |
| D20S21 1 1/2 | 135 | 1.5 | 52 | 103 | A15 plate 188 | TTGGAATCAATGGAGCAAAA | AGCTTTACCCAATGTGTCC | 7 | 8 |
|  |  |  |  | 102 | A1 plate 46 | " | " | " | " |
| 11S-17 F2/B4 | 146 | 3 | 58 | 100 | E4 plate 43 | GCCATGTACCCACCTGAAAAATC | TCAGAACACCCGTGCAGAATTAAG | 13 | 14 |
|  |  |  |  | 101 | J5 plate 118 | " | " | " | " |

The BAC clones of the contig spanning the 20q13 amplicon are listed in Table 2 which provides a cross-reference to the DuPont P1 library described by Shepherd, et al., *Proc. Natl. Acad. Sci. USA*, 92: 2629 (1994). These probes are available commercially from Research Genetics.

In addition, Tables 1 and 2 provide PCR primers for amplifying sequence tagged sites (STSs) for each of the P1 and BAC probes. One of skill in the art would appreciate that using plate coordinates provided above and/or the primers.

Exon Trapping

Exon trapping (see, e.g., Duyk et al., *Proc. Natl. Acad. Sci. USA*, 87: 8995–8999 (1990) and Church et al., *Nature Genetics*, 6: 98–105 (1994)) was performed on the P1 and BAC clones spanning the ≈600 kb minimum common region of amplification and has isolated more than 200 exons.

Analysis of the exons DNA sequence revealed a number of sequence similarities (85% to 96%) to partial cDNA sequences in the expressed sequence data base (dbest) and to a *S. cerevisiae* chromosome XIV open reading frame. Each P1 clone subjected to exon trapping has produced multiple exons consistent with at least a medium density of genes.

Detection of 20q13 Abnormalities

One of skill in the art will appreciate that the clones and sequence information provided herein can be used to detect amplifications, or other chromosomal abnormalities, at 20q13 in a biological sample. Generally the methods involve hybridization of probes that specifically bind one or more nucleic acid sequences of the target amplicon with nucleic acids present in a biological sample or derived from a biological sample.

As used herein, a biological sample is a sample of biological tissue or fluid contains cells in it is desired to screen for chromosomal abnormalities (e.g. amplifications of deletions). In a preferred embodiment, the biological sample is a cell or tissue suspected of being cancerous (transformed). Methods of isolating biological samples are well known to those of skill in the art and include, but are not limited to, aspirations, tissue sections, needle biopsies, and the like. Frequently the sample will be a "clinical sample" which is a sample derived from a patient. It will be recognized that the term "sample" also includes supernatant (containing cells) or the cells themselves from cell cultures, cells from tissue culture and other media in which it may be desirable to detect chromosomal abnormalities.

In a preferred embodiment, a biological sample is prepared by depositing cells, either as single cell suspensions or as tissue preparation, on solid supports such as glass slides and fixed by choosing a fixative which provides the best spatial resolution of the cells and the optimal hybridization efficiency.

Selecting Probes

Any of the P1 probes listed in Table 1 or the BAC probes listed in Table 2 are suitable for use in detecting the 20q13 amplicon. Methods of preparing probes are well known to those of skill in the art (see, e.g. Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987))

The probes are most easily prepared by combining and labeling one or more of the constructs listed in Tables 1 and 2. Prior to use, the constructs are fragmented to provide smaller nucleic acid fragments that easily penetrate the cell and hybridize to the target nucleic acid. Fragmentation can be by any of a number of methods well known to hose of skill in the art. Preferred methods include treatment with a restriction enzyme to selectively cleave the molecules, or alternatively to briefly heat the nucleic acids in the presence of $Mg^{2+}$. Probes are preferably fragmented to an average fragment length ranging from about 50 bp to about 2000 bp, more preferably from about 100 bp to about 1000 bp and most preferably from about 150 bp to about 500 bp.

Alternatively, probes can be produced by amplifying (e.g. via PCR) selected subsequences from the $^{20}$q13 amplicon disclosed herein. The sequences provided herein permit one of skill to select primers that amplify sequences from one or more exons located within the 20q13 amplicon.

Particularly preferred probes include nucleic acids from probes 38, 40, and 79, which corresponds to RMC20C001.

One of skill will appreciate that using the sequence information and clones provided herein, one of skill in the art can isolate the same or similar probes from other human genomic libraries using routine methods (e.g. Southern or Northern Blots).

Labeling Probes

Methods of labeling nucleic acids are well known to those of skill in the art. Preferred labels are those that are suitable for use in in situ hybridization. The nucleic acid probes may be detectably labeled prior to the hybridization reaction. Alternatively, a detectable label which binds to the hybridization product may be used. Such detectable labels include any material having a detectable physical or chemical property and have been well-developed in the field of immunoassays.

As used herein, a "label" is any composition detectable by spectroscopic, photochemical, biochemical, immunochemical, or chemical means. Useful labels in the present invention include radioactive labels (e.g. $^{32}$P, $^{125}$I, $^{14}$C, $^{3}$H, and $^{35}$S), fluorescent dyes (e.g. fluorescein, rhodamine, Texas Red, etc.), electron-dense reagents (e.g. gold), enzymes (as commonly used in an ELISA), colorimetric labels (e.g. colloidal gold), magnetic labels (e.g. Dynabeads™), and the like. Examples of labels which are not directly detected but are detected through the use of directly detectable label include biotin and dioxigenin as well as haptens and proteins for which labeled antisera or monoclonal antibodies are available.

The particular label used is not critical to the present invention, so long as it does not interfere with the in situ hybridization of the stain. However, stains directly labeled with fluorescent labels (e.g. fluorescein-12-dUTP, Texas Red-5-dUTP, etc.) are preferred for chromosome hybridization.

A direct labeled probe, as used herein, is a probe to which a detectable label is attached. Because the direct label is already attached to the probe, no subsequent steps are required to associate the probe with the detectable label. In contrast, an indirect labeled probe is one which bears a moiety to which a detectable label is subsequently bound, typically after the probe is hybridized with the target nucleic acid.

In addition the label must be detectible in as low copy number as possible thereby maximizing the sensitivity of the assay and yet be detectible above any background signal. Finally, a label must be chosen that provides a highly localized signal thereby providing a high degree of spatial resolution when physically mapping the stain against the chromosome. Particularly preferred fluorescent labels include fluorescein-12-dUTP and Texas Red-5-dUTP.

The labels may be coupled to the probes in a variety of means known to those of skill in the art. In a preferred embodiment the nucleic acid probes will be labeled using nick translation or random primer extension (Rigby, et al. *J. Mol. Biol.*, 113: 237 (1977) or Sambrook, et al., *Molecular Cloning-A Laboratory Manual*, Cold Spring Harbor Laboratory, Cold Spring Harbor, N.Y. (1985)).

One of skill in the art will appreciate that the probes of this invention need not be absolutely specific for the targeted 20q13 region of the genome. Rather, the probes are intended to produce "staining contrast". "Contrast" is quantified by the ratio of the probe intensity of the target region of the genome to that of the other portions of the genome. For example, a DNA library produced by cloning a particular chromosome (e.g. chromosome 7) can be used as a stain capable of staining the entire chromosome. The library contains both sequences found only on that chromosome, and sequences shared with other chromosomes. Roughly half the chromosomal DNA falls into each class. If hybridization of the whole library were capable of saturating all of the binding sites on the target chromosome, the target chromosome would be twice as bright (contrast ratio of 2) as the other chromosomes since it would contain signal from the both the specific and the shared sequences in the stain, whereas the other chromosomes would only be stained by the shared sequences. Thus, only a modest decrease in hybridization of the shared sequences in the stain would substantially enhance the contrast. Thus contaminating sequences which only hybridize to non-targeted sequences, for example, impurities in a library, can be tolerated in the stain to the extent that the sequences do not reduce the staining contrast below useful levels.

Detecting the 20q13 Amplicon

As explained above, detection of amplification in the 20q13 amplicon is indicative of the presence and/or prognosis of a large number of cancers. These include, but are not limited to breast, ovary, bladder, head and neck, and colon.

In a preferred embodiment, a 20q13 amplification is detected through the hybridization of a probe of this invention to a target nucleic acid (e.g. a chromosomal sample) in which it is desired to screen for the amplification. Suitable hybridization formats are well known to those of skill in the art and include, but are not limited to, variations of Southern Blots, in situ hybridization and quantitative amplification methods such as quantitative PCR (see, e.g. Sambrook, supra., Kallioniemi et al., *Proc. Natl Acad Sci USA*, 89: 5321–5325 (1992), and *PCR Protocols, A Guide to Methods and Applications*, Innis et al., Academic Press, Inc. N.Y., (1990)).

In situ Hybridization

In a preferred embodiment, the 20q13 amplicon is identified using in situ hybridization. Generally, in situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments. The reagent used in each of these steps and their conditions for use vary depending on the particular application.

In some applications it is necessary to block the hybridization capacity of repetitive sequences. In this case, human genomic DNA is used as an agent to block such hybridization. The preferred size range is from about 200 bp to about 1000 bases, more preferably between about 400 to about 800 bp for double stranded, nick translated nucleic acids.

Hybridization protocols for the particular applications disclosed here are described in Pinkel et al. *Proc. Natl. Acad. Sci. USA*, 85: 9138–9142 (1988) and in EPO Pub. No. 430,402. Suitable hybridization protocols can also be found in *Methods o\in Molecular Biology Vol. 33: In Situ Hybridization Protocols*, K. H. A. Choo, ed., Humana Press, Totowa, N.J., (1994). In a particularly preferred embodiment, the hybridization protocol of Kallioniemi et al., *Proc. Natl Acad Sci USA*, 89: 5321–5325 (1992) is used.

Typically, it is desirable to use dual color FISH, in which two probes are utilized, each labelled by a different fluorescent dye. A test probe that hybridizes to the region of interest is labelled with one dye, and a control probe that hybridizes to a different region is labelled with a second dye. A nucleic acid that hybridizes to a stable portion of the chromosome of interest, such as the centromere region, is often most useful as the control probe. In this way, differences between efficiency of hybridization from sample to sample can be accounted for.

The FISH methods for detecting chromosomal abnormalities can be performed on nanogram quantities of the subject nucleic acids. Paraffin embedded tumor sections can be used, as can fresh or frozen material. Because FISH can be applied to the limited material, touch preparations prepared from uncultured primary tumors can also be used (see, e.g., Kallioniemi, A. et al., *Cytogenet. Cell Genet.* 60: 190–193 (1992)). For instance, small biopsy tissue samples from tumors can be used for touch preparations (see, e.g., Kallioniemi, A. et al., *Cytogenet. Cell Genet.* 60: 190–193 (1992)). Small numbers of cells obtained from aspiration biopsy or cells in bodily fluids (e.g., blood, urine, sputum and the like) can also be analyzed. For prenatal diagnosis, appropriate samples will include amniotic fluid and the like.

Southern Blots

In a Southern Blot, a genomic or cDNA (typically fragmented and separated on an electrophoretic gel) is hybridized to a probe specific for the target region. Comparison of the intensity of the hybridization signal from the probe for the target region (e.g., 20q13) with the signal from a probe directed to a control (non amplified) such as centromeric DNA, provides an estimate of the relative copy number of the target nucleic acid.

Kits Containing 20q13 Amplicon Probes

This invention also provides diagnostic kits for the detection of chromosomal abnormalities at 20q13. In a preferred embodiment, the kits include one or more probes to the 20q13 amplicon described herein. The kits can additionally include blocking probes, instructional materials describing how to use the kit contents in detecting 20q13 amplicons. The kits may also include one or more of the following: various labels or labeling agents to facilitate the detection of the probes, reagents for the hybridization including buffers, a metaphase spread, bovine serum albumin (BSA) and other blocking agents, sampling devices including fine needles, swabs, aspirators and the like, positive and negative hybridization controls and so forth.

EXAMPLES

The following examples are offered to illustrate, but not to limit the present invention.

Example 1

PROGNOSTIC IMPLICATIONS OF AMPLIFICATION OF CHROMOSOMAL REGION 20q13 IN BREAST CANCER

Patients and tumor material

Tumor samples were obtained from 152 women who underwent surgery for breast cancer between 1987 and 1992 at the Tampere University or City Hospitals. One hundred and forty-two samples were from primary breast carcinomas and 11 from metastatic tumors. Specimens from both the primary tumor and a local metastasis were available from one patient. Ten of the primary tumors that were either in situ or mucinous carcinomas were excluded from the material, since the specimens were considered inadequate for FISH studies. Of the remaining 132 primary tumors, 128 were invasion ductal and 4 lobular carcinomas. The age of the patients ranged from 29 to 92 years (mean 61). Clinical follow-up was available from 129 patients. Median follow-up period was 45 months (range 1.4–1.77 months). Radiation therapy was given to 77 of the 129 patients (51 patients with positive and 26 with negative lymph nodes), and systemic adjuvant therapy to 36 patients (33 with endocrine and 3 with cytotoxic chemotherapy). Primary tumor size and axillary node involvement were determined according to the tumor-node metastasis (TNM) classification. The histopathological diagnosis was evaluated according to the World Health Organization (11). The carcinomas were graded on the basis of the tubular arrangement of cancer cells, nuclear atypia, and frequency of mitotic or hyperchromatic nuclear figures according to Bloom and Richardson, *Br. J. Cancer*, 11: 359–377 (1957).

Surgical biopsy specimens were frozen at −70° C. within 15 minutes of removal. Cryostat sections (5–6 µm) were prepared for intraoperative histopathological diagnosis, and additional thin sections were cut for immunohistochemical studies. One adjacent 200 µm thick section was cut for DNA flow cytometric and FISH studies.

Cell preparation for FISH

After histological verification that the biopsy specimens contained a high proportion of tumor cells, nuclei were isolated from 200 µm frozen sections according to a modified Vindelov procedure for DNA flow cytometry, fixed and dropped on slides for FISH analysis as described by Hyytinen et al., *Cytometry* 16: 93–99 (1994). Foreskin fibroblasts were used as negative controls in amplification studies and were prepared by harvesting cells at confluency to obtain G1 phase enriched interphase nuclei. All samples were fixed in methanol-acetic-acid (3:1).

Probes

Five probes mapping to the 20q13 region were used (see Stokke, et al., *Genomics*, 26: 134–137 (1995)). The probes included P1-clones for melanocortin-3-receptor (probe MC3R, fractional length from p-arm telomere (Flpter 0.81) and phosphoenolpyruvate carboxy kinase (PCK, Flpter 0.84), as well as anonymous cosmid clones RMC20C026 (Flpter 0.79). In addition, RMC20C001 (Flpter 0.825) and RMC20C030 (Flpter 0.85) were used. Probe RMC20C001 was previously shown to define the region of maximum amplification (Tanner et al., *Cancer Res*, 54: 4257–4260 (1994)). One cosmid probe mapping to the proximal p-arm, RMC20C038 (FLpter 0.237) was used as a chromosome-specific reference probe. Test probes were labeled with biotin-14-dATP and the reference probe with digoxigenin-11-dUTP using nick translation (Kallioniemi et al., *Proc. Natl Acad Sci USA*, 89: 5321–5325 (1992)).

Fluorescence in situ hybridization

Two-color FISH was performed using biotin-labeled 20q13-specific probes and digoxigenin-labelled 20p reference probe essentially as described (Id.). Tumor samples were postfixed in 4% paraformaldtheyde/phosphate-buffered saline for 5 min at 4C prior to hybridization, dehydrated in 70%, 85% and 100% ethanol, air dried, and incubated for 30 min at 80° C. Slides were denatured in a 70% formamide/2× standard saline citrate solution at 72°–74° C. for 3 min, followed by a proteinase K digestion (0.5 µg/ml). The hybridization mixture contained 18 ng of each of the labeled probes and 10 µg human placental DNA. After hybridization, the probes were detected immunochemically with avidin-FITC and anti-digoxigenin Rhodamine. Slides were counterstained with 0.2 µM 4,6-diamidino-2-phenylindole (DAPI) in an antifade solution.

Fluorescence microscopy and scoring of signals in interphase nuclei

A Nikon fluorescence microscope equipped with double band-bass filters (Chromatechnology, Brattleboro, Vt., USA) and 63× objective (NA 1.3) was used for simultaneous visualization of FITC and Rhodamine signals. At least 50 non-overlapping nuclei with intact morphology based on the DAPI counterstaining were scored to determine the number of test and reference probe hybridization signals. Leukocytes infiltrating the tumor were excluded from analysis. Control hybridizations to normal fibroblast interphase nuclei were done to ascertain that the probes recognized a single copy target and that the hybridization efficiencies of the test and reference probes were similar.

The scoring results were expressed both as the mean number of hybridization signals per cell and as mean level of amplification (=mean of number of signals relative to the number of reference probe signals).

DNA flow cytometry and steroid receptor analyses

DNA flow cytometry was performed from frozen 200 µm sections as described by Kallioniemi, *Cytometry* 9: 164–169 (1988). Analysis was carried out using an EPICS C flow cytometer (Coulter Electronics Inc., Hialeah, Fla., USA) and the MultiCycle program (Phoenix Flow Systems, San Diego, Calif., USA). DNA-index over 1.07 (in over 20% of cells) was used as a criterion for DNA aneuploidy. In DNA aneuploid histograms, the S-phase was analyzed only from the aneuploid clone. Cell cycle evaluation was successful in 86% (108/126) of the tumors.

Estrogen (ER) and progesterone (PR) receptors were detected immunohistochemically, from cryostat sections as previously described (17). The staining results were semi-quantitatively evaluated and a histoscore greater than or equal to 100 was considered positive for both ER and PR (17).

Statistical Methods

Contingency tables were analyzed with Chi square test for trend. Association between S-phase fraction (continuous variable) and 20q13 amplification was analyzed with Kruskal-Wallis test. Analysis of disease-free survival was performed using the BMDPIL program and Mautel-Cox test and Cox's proportional hazards model (BMDP2L program) was used in multivariate regression analysis (Dixon *BMDP Statistical Software*. London, Berkeley, Los Angeles: University of California Press, (1981)).

Amplification of 20q13 in primary breast carcinomas by fluorescence in situ hybridization The minimal region probe RMC20C001 was used in FISH analysis to assess the 20q13 amplification. FISH was used to analyze both the total number of signals in individual tumor cells and to determine the mean level of amplification (mean copy number with the RMC20C001 probe relative to a 20p-reference probe). In addition, the distribution of the number of signals in the tumor nuclei was also assessed. Tumors were classified into three categories: no, low and high level of amplification. Tumors classified as not amplified showed less than 1.5 than 1.5 fold-copy number of the RMC20C001 as compared to the p-arm control. Those classified as having low-level amplification had 1.5–3-fold average level of amplification. Tumors showing over 3-fold average level of amplification were classified as highly amplified.

The highly amplified tumors often showed extensive intratumor heterogeneity with up to 40 signals in individual tumor cells. In highly amplified tumors, the RMC20C001 probe signals were always arranged in clusters by FISH, which indicates location of the amplified DNA sequences in close proximity to one another e.g. in a tandem array. Low level 20q13 amplification was found in 29 of the 132 primary tumors (22%), whereas nine cases (6.8%) showed high level amplification. The overall prevalence of increased copy number in 20q13 was thus 29% (38/132).

Defining the minimal region of amplification

The average copy number of four probes flanking RMC20C001 was determined in the nine highly amplified tumors. The flanking probes tested were malanocortin-3-receptor (MC3R, FLpter 0.81), phosphoenolpyruvate carboxykinase (PCK, 0.84), RMC20C026 (0.79) and RMC20C030 (0.85). The amplicon size and location varied slightly from one tumor to another but RMC20C001 was the only probe consistently highly amplified in all nine cases.

Association of 20q13 amplification with pathological and biological features

The 20q13 amplification was significantly associated with high histologic grade of the tumors (p=0.01). This correlation was seen both in moderately and highly amplified tumors (Table 1). Amplification of 20q13 was also significantly associated with aneuploidy as determined by DNA flow cytometry (p=0.01, Table 1.) The mean cell proliferation activity, measured as the percentage of cells in the S-phase fraction, increased (p=0.0085 by Kruskal-Wallis test) with the level of amplification in tumors with no, low and high levels of amplification (Table 1). No association was found with the age of the patient, primary tumor size, axillary nodal or steroid hormone-receptor status (Table 1).

TABLE 1

Clinicopathological correlations of amplification at chromosomal region 20q13 in 132 primary breast cancers.

| | 20q13 amplification status | | | |
|---|---|---|---|---|
| Pathobiologic feature | NO Number of patients (%) | LOW LEVEL Number of patients (%) | HIGH LEVEL Number of patients (%) | p-value[1] |
| All primary tumors | 94 (71%) | 29 (22%) | 9 (6.8%) | |
| Age of patients | | | | |
| <50 years | 17 (65%) | 6 (23%) | 3 (12%) | |
| ≥50 years | 77 (73%) | 23 (22%) | 6 (5.7%) | .39 |
| Tumor size | | | | |
| <2 cm | 33 (79%) | 7 (17%) | 2 (4.8%) | |
| ≥2 cm | 58 (67%) | 22 (25%) | 7 (8.0%) | |
| Nodal status | | | | |
| Negative | 49 (67%) | 19 (26%) | 5 (6.8%) | |

TABLE 1-continued

Clinicopathological correlations of amplification at chromosomal region 20q13 in 132 primary breast cancers.

| | 20q13 amplification status | | | |
|---|---|---|---|---|
| Pathobiologic feature | NO Number of patients (%) | LOW LEVEL Number of patients (%) | HIGH LEVEL Number of patients (%) | p-value[1] |
| Positive | 41 (75%) | 10 (18%) | 4 (7.3%) | .41 |
| Histologic grade | | | | |
| I-II | 72 (76%) | 18 (19%) | 5 (5.3%) | |
| III | 16 (52%) | 11 (35%) | 4 (13%) | |
| | | | | .01 |
| Estrogen receptor status | | | | |
| Negative | 30 (67%) | 10 (22%) | 5 (11%) | |
| Positive | 59 (72%) | 19 (23%) | 4 (4.9%) | |
| | | | | .42 |
| Progesterone receptor status | | | | |
| Negative | 5.7 (69%) | 20 (24%) | 6 (7.2%) | |
| Positive | 32 (74%) | 8 (19%) | 3 (7.0%) | |
| | | | | .53 |
| DNA ploidy | | | | |
| Diploid | 45 (82%) | 8 (14.5%) | 2 (3.6%) | .01 |
| Aneuploid | 44 (62%) | 20 (28%) | 7 (10%) | |
| S-phase fraction | mean ± SD | mean ± SD | mean ± SD | .0085[1] |
| (%) | 9.9 ± 7.2 | 12.6 ± 6.7 | 19.0 ± 10.5 | |

[1]Kruskal-Wallis Test.

Relationship between 20q13 amplification and disease-free survival

Disease-free survival of patients with high-level 20q13 amplification was significantly shorter than for patients with no or only low-level amplification (p-0.04). Disease-free survival of patients with moderately amplified tumors did not differ significantly from that of patients with no amplification. Among the node-negative patients (n=79), high level 20q13 amplification was a highly significant prognostic factor for shorter disease-free survival (p=0.002), even in multivariate Cox's regression analysis (p=0.026) after adjustment for tumor size ER, PR grade, ploidy and S-phase fraction.

20q13 amplification in metastatic breast tumors

Two of 11 metastatic breast tumors had low level and one high level 20q13 amplification. Thus, the overall prevalence (27%) of increased 20q13 copy number in metastatic tumors was a similar to that observed in the primary tumors. Both a primary and a metastatic tumor specimens were available from one of the patients. This 29-year old patient developed a pectoral muscle infiltrating metastasis eight months after total mastectomy. The patient did not receive adjuvant or radiation therapy after mastectomy. The majority of tumor cells in the primary tumor showed a low level amplification, although individual tumor cells (less than 5% of total) contained 8–20 copies per cell by FISH. In contrast, all tumor cells from metastasis showed high level 20q13 amplification (12–50 copies per cell). The absolute copy number of the reference probe remained the same suggesting that high level amplification was not a result of an increased degree of aneuploidy.

Diagnostic and Prognostic Value of the 20q13 Amplification

The present findings suggest that the newly-discovered 20q13 amplification may be an important component of the genetic progression pathway of certain breast carcinomas.

Specifically, the foregoing experiments establish that: 1) High-level 20q13 amplification, detected in 7% of the tumors, was significantly associated with decreased disease-free survival in node-negative breast cancer patients, as well as with indirect indicators of high-malignant potential, such as high grade and S-phase fraction. 2) Low-level amplification, which was much more common, was also associated with clinicopathological features of aggressive tumors, but was not prognostically significant. 3) The level of amplification of RMC20C001 remains higher than amplification of nearby candidate genes and loci indicating that a novel oncogene is located in the vicinity of RMC20C001.

High-level 20q13 amplification was defined by the presence of more than 3-fold higher copy number of the 20q13 amplification is somewhat lower than the amplification frequencies reported for some of the other breast cancer oncogenes, such as ERBB2 (17q12) and Cyclin-D (11q13) (Borg et al., *Oncogene*, 6: 137–143 (1991), Van de Vijver et al. *Adv. Canc. Res.*, 61: 25–56 (1993)). However, similar to what has been previously found with these other oncogenes (Swab, et al., *Genes Chrom. Canc.*, 1: 181–193 (1990), Borg et al., supra.), high-level 20q13 amplification was more common in tumors with high grade or high S-phase fraction and in cases with poor prognosis. Although only a small number of node-negative patients was analyzed, our results suggest that 20q13 amplification might have independent role as a prognostic indicator. Studies to address this question in large patient materials are warranted. Moreover, based on these survival correlations, the currently unknown, putative oncogene amplified in this locus may confer an aggressive phenotype. Thus, cloning of this gene is an important goal. Based on the association of amplification with highly proliferative tumors one could hypothesize a role for this gene in the growth regulation of the cell.

The role of the low-level 20q13 amplification as a significant event in tumor progression appears less clear. Low-level amplification was defined as 1.5–3-fold increased average copy number of the 20q13 probe relative to the p-arm control. In addition, these tumors characteristically lacked individual tumor cells with very high copy numbers, and showed a scattered, not clustered, appearance of the signals. Accurate distinction between high and low level 20q13 amplification can only be reliably done by FISH, whereas Southern and slot blot analyses are likely to be able to detect only high-level amplification, in which substantial elevation of the average gene copy number takes place. This distinction is important, because only the high amplified tumors were associated with adverse clinical outcome. Tumors with low-level 20q13 amplification appeared to have many clinicopathological features that were in between of those found for tumors with no and those with high level amplification. For example, the average tumor S-phase fraction was lowest in the non-amplified tumors and highest in the highly amplified tumors. One possibility is that low-level amplification precedes the development of high level amplification. This has been shown to be the case, e.g., in the development of drug resistance-gene amplification in vitro (Stark, *Adv. Canc. Res.*, 61: 87–113 (1993)). Evidence supporting this hypothesis was found in one of our patients, whose local metastasis contained a much higher level of 20q13 amplification than the primary tumor operated 8 months earlier.

Finally, our previous paper reported a 1.5 Mb critical region defined by RMC20C001 probe and exclusion of candidate genes in breast cancer cell lines and in a limited number of primary breast tumors. Results of the present study confirm these findings by showing conclusively in a larger set of primary tumors that the critical region of amplification is indeed defined by this probe.

The present data thus suggest that the high-level 20q13 amplification may be a significant step in the progression of certain breast tumors to a more malignant phenotype. The clinical and prognostic implications of 20q13 amplification are striking and location of the minimal region of amplification at 20q13 has now been defined.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

---

What is claimed is:

1. A method of detecting a chromosome abnormality at about position FLpter 0.825 on human chromosome 20, the method comprising:

contacting a chromosome sample from a patient with a composition consisting essentially of one or more labeled nucleic acid probes each of which binds selectively to a target polynucleotide sequence on human chromosome 20 under conditions in which the probe forms a stable hybridization complex with the target sequence, wherein said target polynucleotide sequence comprises about 600 kilobases flanked by and including DuPont P1 library P1 clones 3 and 12, identified by single clone addresses 12e11 and 42c2 respectively; and detecting the hybridization complex.

2. The method of claim 1, wherein the probe comprises a nucleic acid that specifically hybridizes under stringent conditions to a clone from the DuPont P1 library wherein said clone is selected from the group consisting of 1228e, 821g, 1167f, 276h, 1418f, 1199d2, 1020c, 1232d, 1081b9, 370d, 416f, 480b, 493c, 429f, 264c, 142e, 921a, 1139g, 401a, and 630c, or to a clone from a Research Genetics BAC library wherein said clone is selected from the group consisting of BAC 99 (L11 plate 146), BAC 97 (E8 plate 183), BAC 95 (H15 plate 140), BAC 103 (A15 plate 188), BAC 102 (A1 plate 46), BAC 101 (J5 plate 118), and BAC 100 (E4 plate 43).

3. The method of claim 1, wherein the step of detecting the hybridization complex comprises determining the copy number of the target sequence.

4. The method of claim 1, wherein the probe is labeled with digoxigenin or biotin.

5. The method of claim 1, wherein the hybridization complex is detected in interphase nuclei in the sample.

6. The method of claim 1, wherein the chromosome abnormality is an amplification.

7. The method of claim 1, wherein the probes are labeled with digoxigenin or biotin.

8. The method of claim 1, wherein the step of detecting the hybridization complexes is carried out by detecting a fluorescent label.

9. The method of claim 8, wherein the fluorescent label is FITC.

10. The method of claim 1, further comprising contacting the sample with a reference probe which binds selectively to a chromosome 20 centromere.

11. A composition comprising a labeled nucleic acid probe which binds selectively to a target polynucleotide sequence on human chromosome 20, wherein said probe comprises a nucleic acid that specifically hybridizes under stringent conditions to a clone from a DuPont P1 library wherein said clone is selected from the group consisting of 1228e, 821g, 1167f, 276h, 416f, 480b, 493c, 429f, 264c, 142e, 921a, 1139g, 401a, and 630c, or to a clone from a Research Genetics BAC library wherein said clone is selected from the group consisting of BAC 99 (L11plate 146), BAC 97 (E8 plate 183), BAC 95 (H15 plate 140), BAC 103 (A15 plate 188), BAC 102 (A1 plate 46), BAC 101 (J5 plate 118), and BAC 100 (4 plate 43).

12. The composition of claim 11, wherein the probe is labelled with digoxigenin or biotin.

13. The composition of claim 11 wherein the probe comprises one or more nucleic acids comprising a clone from a DuPont P1 library wherein said clone is selected from the group consisting of 1228e, 821g, 1167f, 276h, 416f, 480b, 493c, 429f, 264c, 142e, 921a, 1139g, 401a, and 630c or a clone from a Research Genetics BAC library wherein said clone is selected from the group consisting of BAC 99 (L11 plate 146), BAC 97 (E8 plate 183), BAC 95 (H15 plate 140), BAC 103 (A15 plate 188), BAC 102 (A1 plate 46), BAC 101 (J5 plate 118), and BAC 100 (E4 plate 43).

14. A kit for the detection of a chromosomal abnormality on human chromosome 20, the kit comprising a compartment which contains a labeled nucleic acid probe which binds selectively to a target polynucleotide sequence on human chromosome 20, wherein said probe comprises a nucleic acid that specifically hybridizes under stringent conditions to a clone from a DuPont P1 library wherein said clone is selected from the group consisting of 1228e, 821g, 1167f, 276h, 416f, 480b, 493c, 429f, 264c, 142e, 921a, 1139g, 401a, and 630c, or to a clone from a Research Genetics BAC library wherein said clone is selected from the group consisting of BAC 99 (L11 plate 146), BAC 97 (E8 plate 183), BAC 95 (H 15 plate 140), BAC 103 (A15 plate 188), BAC 102 (A1 plate 46), BAC 101 (J5 plate 118), and BAC 100 (E4 plate 43).

15. The kit of claim 14, wherein label is selected from the group consisting of digoxigenin and biotin.

16. The kit of claim 14, further comprising a reference probe specific to a sequence in the centromere of chromosome 20.

17. The kit of claim 14, further comprising Texas red avidin and biotin-labeled goat anti-avidin antibodies.

18. The method of claim 2, wherein said clone is 1228e.

19. The method of claim 2, wherein said clone is 821g.

20. The method of claim 2, wherein said clone is 1167f.

21. The method of claim 2, wherein said clone is 276h.

22. The method of claim 2, wherein said clone is 1418f.

23. The method of claim 2, wherein said clone is 1199d2.

24. The method of claim 2, wherein said clone is 1020c.

25. The method of claim 2, wherein said clone is 1232d.

26. The method of claim 2, wherein said clone is 1081b9.

27. The method of claim 2, wherein said clone is 370d.

28. The method of claim 2, wherein said clone is 416f.

29. The method of claim 2, wherein said clone is 480b.

30. The method of claim 2, wherein said clone is 493c.

31. The method of claim 2, wherein said clone is 429f.

32. The method of claim 2, wherein said clone is 264c.

33. The method of claim 2, wherein said clone is 142e.

34. The method of claim 2, wherein said clone is 921a.

35. The method of claim 2, wherein said clone is 1139g.

36. The method of claim 2, wherein said clone is 401a.

37. The method of claim 2, wherein said clone is 630c.

38. The method of claim 2, wherein said clone is BAC 99 (L11 plate 146).

39. The method of claim 2, wherein said clone is BAC 97 (E8 plate 183).

40. The method of claim 2, wherein said clone is BAC 95 (H15 plate 140).

41. The method of claim 2, wherein said clone is BAC 103 (A15 plate 188).

42. The method of claim 2, wherein said clone is BAC 102 (A1 plate 46).

43. The method of claim 2, wherein said clone is BAC 101 (J5 plate 118).

44. The method of claim 2, wherein said clone is BAC 100 (E4 plate 43).

* * * * *

UNITED STATES PATENT AND TRADEMARK OFFICE
CERTIFICATE OF CORRECTION

PATENT NO. : 5,801,021
DATED : September 1, 1998
INVENTOR(S) : Joe W. Gray, et. al.

It is certified that error appears in the above-identified patent and that said Letters Patent is hereby corrected as shown below:

In claim 11, column 37, line 29, delete "4" and insert --E4--

In claim 13, column 37, line 39, delete "183" and insert --133--.

In claim 14, column 38, line 4, delete "H 15" and insert --H15--.

Signed and Sealed this

Ninth Day of March, 1999

Attest:

Attesting Officer

Q. TODD DICKINSON

Acting Commissioner of Patents and Trademarks

UNITED STATES PATENT AND TRADEMARK OFFICE
CERTIFICATE OF CORRECTION

PATENT NO.     : 5,801,021
DATED          : September 1, 1998
INVENTOR(S)    : Joe W. Grey et al.

It is certified that error appears in the above-identified patent and that said Letters Patent is hereby corrected as shown below:

Column 38,
Line 37, delete "183" and insert -- 133 --.

Signed and Sealed this

Seventeenth Day of February, 2004

JON W. DUDAS
*Acting Director of the United States Patent and Trademark Office*